US012765475B2

(12) United States Patent
Liu et al.

(10) Patent No.: US 12,765,475 B2
(45) Date of Patent: Oct. 20, 2026

(54) HAND-HELD VAPOR PRESSURE DEFICIT MEASURING AND CONTROLLING DEVICE AND METHOD

(71) Applicant: AC Infinity Inc., City of Industry, CA (US)

(72) Inventors: Jimmy Liu, Brea, CA (US); Daniel Yu Hsu, Upland, CA (US); Wilbur Y. Cheng, Chino Hills, CA (US); Wei Ying Shao, Alhambra, CA (US)

(73) Assignee: AC Infinity Inc., City of Industry (CA)

( * ) Notice: Subject to any disclaimer, the term of this patent is extended or adjusted under 35 U.S.C. 154(b) by 334 days.

(21) Appl. No.: 18/641,287

(22) Filed: Apr. 19, 2024

(65) Prior Publication Data

US 2025/0324929 A1 Oct. 23, 2025

(51) Int. Cl.

| | |
|---|---|
| ***A01G 9/26*** | (2006.01) |
| ***A01G 9/24*** | (2006.01) |
| ***G01L 13/06*** | (2006.01) |
| ***G01N 33/00*** | (2006.01) |
| *G01L 19/00* | (2006.01) |

(52) U.S. Cl.

CPC ............... *A01G 9/26* (2013.01); *A01G 9/246* (2013.01); *G01L 13/06* (2013.01); *G01N 33/0098* (2013.01); *G01L 2019/0053* (2013.01)

(58) Field of Classification Search

CPC ...... A01G 9/246; A01G 9/26; G01N 33/0098; G01L 13/06; G01L 19/00

USPC ................. 700/300; 236/44; 261/129; 47/17

See application file for complete search history.

(56) References Cited

U.S. PATENT DOCUMENTS

| | | | | | |
|---|---|---|---|---|---|
| 4,420,265 | A * | 12/1983 | Everest | ..................... | G01J 5/06 374/161 |
| 4,494,881 | A * | 1/1985 | Everest | ................. | G01J 5/0802 250/353 |
| 4,876,647 | A † | 10/1989 | Gardner | | |

(Continued)

FOREIGN PATENT DOCUMENTS

| | | | | |
|---|---|---|---|---|
| CA | 2883489 A1 * | 3/2014 | ............. | A01G 9/246 |
| CN | 103234691 B † | 2/2015 | | |

(Continued)

*Primary Examiner* — Crystal J Barnes-Bullock
(74) *Attorney, Agent, or Firm* — NKL Law; Allen Xue

(57) ABSTRACT

A hand-held VPD measuring and controlling device for plant cultivation is disclosed. The hand-held vapor pressure deficit (VPD measuring and controlling device includes: a device body with a barrel, a handle, and a trigger; a screen for displaying information on one end of the barrel of the device body; a control module with a processing unit located inside the device body; a laser beam transmitter emitting a laser beam located inside the device body, the direction of the laser beam emitted by the laser transmitter is parallel to the direction of the barrel of the device body; an infrared temperature sensor for measuring a temperature value at a location pointed by the laser beam. When the trigger is pulled, the temperature value $T_{LEAF}$ at the location pointed by the laser beam is measured by the infrared temperature sensor and the temperature value $T_{LEAF}$ is transmitted to the control module in real time.

20 Claims, 6 Drawing Sheets

(56) References Cited

U.S. PATENT DOCUMENTS

| | | | | |
|---|---|---|---|---|
| 9,107,354 | B2 * | 8/2015 | Martin | A01G 25/167 |
| 9,439,367 | B2 * | 9/2016 | Abhyanker | G05D 1/0038 |
| 11,406,057 | B2 * | 8/2022 | Zhang | G01D 21/02 |
| 2020/0037522 | A1 * | 2/2020 | DeJarnette | A01G 27/003 |
| 2024/0397880 | A1 * | 12/2024 | Meersand | A01G 9/26 |

FOREIGN PATENT DOCUMENTS

| | | | | | |
|---|---|---|---|---|---|
| CN | 105230341 | A | * | 1/2016 | A01G 18/60 |
| CN | 106442333 | A | * | 2/2017 | G01N 21/17 |
| CN | 207851560 | U | * | 9/2018 | |
| CN | 111406542 | A | * | 7/2020 | A01G 9/26 |
| CN | 117288251 | A | * | 12/2023 | G01D 21/02 |
| EP | 2706331 | A1 | † | 3/2014 | |
| KR | 20180006735 | A | * | 1/2018 | H04N 5/33 |
| KR | 20220136016 | A | * | 10/2022 | A01G 1/69 |
| KR | 20230115213 | A | * | 8/2023 | F24H 9/02 |

* cited by examiner
† cited by third party

VPD gun

HAND-HELD VAPOR PRESSURE DEFICIT MEASURING AND CONTROLLING DEVICE AND METHOD

FIELD OF INVENTION

This invention relates to vapor pressure deficit measuring and controlling device and method for plant cultivation, and in particular to vapor pressure deficit measuring and controlling device and method for plant cultivation to optimize the plant cultivation environment.

BACKGROUND OF INVENTION

Commercial indoor plant growers use temperature and humidity parameters to fine tune their cultivation environment to increase plant yield, but for emerging residential indoor growers, they often lack the tools needed to maintain an optimal growing environment with temperature and humidity. Such tools include for example, humidifier, dehumidifier, air conditioner, and heater.

An object of the invention is to provide an improved and efficient device and method to control the plant cultivation environment using vapor pressure deficit ("VPD" hereafter.) By utilizing VPD, residential growers can eliminate at least one or two of the above-mentioned expensive equipment's while still maintaining the same optimal cultivation environment as long as the temperature and humidity of the cultivation space does not reach extreme levels. This is because both the heater and the dehumidifier are able to increase VPD, while both the air conditioner and humidifier are able to decrease VPD.

SUMMARY OF INVENTION

Vapor Pressure Deficit, or VPD, plays a crucial role in plant indoor cultivation, especially high valued plants, such as cannabis. VPD is the difference between moisture that is currently in the environment air and how much moisture the environment air can hold at saturation, or dew point under certain conditions.

According to an embodiment of the invention, a hand-held VPD measuring and controlling device for plant cultivation is disclosed. The hand-held VPD measuring and controlling device includes: a device body with a barrel, a handle and a trigger; a screen for displaying information on one end of the barrel of the device body; a control module with a processing unit located inside the device body; a laser beam transmitter emitting a laser beam located inside the device body, the direction of the laser beam emitted by the laser beam transmitter is parallel to the direction of the barrel of the device body; an infrared temperature sensor for measuring a temperature value at a location pointed by the laser beam, when the trigger is pulled, the temperature value $T_{LEAF}$ at the location pointed by the laser beam is measured by the infrared temperature sensor and the temperature value $T_{LEAF}$ is transmitted to the control module in real time; an environmental temperature-humidity sensor for sensing an environmental temperature value $T_{ENV}$ and an environmental relative humidity value $RH_{ENV}$ within a plant cultivation environment, the environmental temperature value $T_{ENV}$ and the environmental relative humidity value $RH_{ENV}$ are transmitted to the control module in real time, and a leaf VPD value $VPD_{LEAF}$ is calculated from the temperature value $T_{LEAF}$, the environmental temperature value $T_{ENV}$ and the environmental relative humidity value $RH_{ENV}$ by the processing unit of the control module, an environmental VPD value $VPD_{ENV}$ IS calculated from the environmental temperature value $T_{ENV}$ and the environmental relative humidity value $RH_{ENV}$ by the processing unit of the control module; the temperature value $T_{LEAF}$, the environmental temperature value $T_{ENV}$, the environmental relative humidity value $RH_{ENV}$, the leaf VPD value $VPD_{LEAF}$, the environmental VPD value $VPD_{ENV}$ are displayed on the screen.

According to an embodiment of the invention, the hand-held VPD measuring and controlling device for plant cultivation further includes: a wireless module for wirelessly communicating information with other devices. According to an embodiment of the invention, one of heaters, dehumidifiers, humidifiers, or air conditioners inside the plant cultivation environment can be selected on a remote controller to be remotely controlled. According to an embodiment of the invention, the leaf VPD value $VPD_{LEAF}$ is compared with a pre-determined VPD threshold value $VPD_\theta$ to determine running modes of heaters, dehumidifiers, humidifiers, or air conditioners inside the plant cultivation environment to adjust the leaf VPD value $VPD_{LEAF}$ within the plant cultivation environment, and the remote controller wirelessly transmits control signals to heaters, dehumidifiers, humidifiers, or air conditioners inside the plant cultivation environment to adjust the environmental temperature value $T_{ENV}$, or the environmental relative humidity value $RH_{ENV}$ within the plant cultivation environment. According to an embodiment of the invention, when the trigger is triggered, the updated temperature value $T_{LEAF}$ is measured the temperature-humidity sensor senses an updated environmental temperature value $T_{ENV}$ and an updated environmental relative humidity value $RH_{ENV}$ within the plant cultivation environment; the updated temperature value $T_{LEAF}$, the updated environmental temperature value $T_{ENV}$ and the updated environmental relative humidity value $RH_{ENV}$ are transmitted to the control module; and an updated leaf VPD value $VPD_{LEAF}$ is calculated from the updated temperature value $T_{LEAF}$, the updated environmental temperature value $T_{ENV}$ and the updated environmental relative humidity value $RH_{ENV}$ by the processing unit of the control module.

According to an embodiment of the invention, the updated leaf VPD value $VPD_{LEAF}$ is compared with the pre-determined VPD threshold value $VPD_\theta$ again to adjust the running modes of the heaters, dehumidifiers, humidifiers, or air conditioners inside the plant cultivation environment to adjust the leaf VPD value $VPD_{LEAF}$ within the plant cultivation environment; and the control module wirelessly transmits control signals to the heaters, dehumidifiers, humidifiers, or air conditioners inside the plant cultivation environment to adjust the environmental temperature value $T_{ENV}$, or the environmental relative humidity value $RH_{ENV}$ within the plant cultivation environment. According to an embodiment of the invention, the hand-held VPD measuring and controlling device for plant cultivation further includes a connector for connecting with an external digital device with touch screen, the hand-held VPD measuring and controlling device can be controlled by the external digital device with touch screen.

According to an embodiment of the invention, a pistol shaped hand-held VPD measuring and controlling device for plant cultivation is disclosed. The pistol shaped hand-held VPD measuring and controlling device includes: a muzzle, a barrel, a grip and a trigger; a battery unit for providing electric power to the pistol shaped hand-held VPD measuring and controlling device, the battery unit is located in the grip of the pistol shaped hand-held VPD measuring and controlling device; an infrared receiving device for measuring a temperature value $T_{LEAF}$, the infrared receiving device receiving infrared beams through the muzzle and along a direction of the barrel of the pistol shaped hand-held VPD measuring and controlling device; a laser transmitter used to emit a laser beam parallel to the direction of the barrel and passes through the muzzle, and an infrared receiving device measures the temperature value $T_{LEAF}$ at the point where the laser beam is pointed to; an IO interface for input and output of control information and status information; a temperature-humidity sensor for sensing an environmental temperature value $T_{ENV}$ and an environmental relative humidity value $RH_{ENV}$ within an plant cultivation environment, a leaf VPD value $VPD_{LEAF}$ is calculated from the environmental temperature value $T_{ENV}$ and the environmental relative humidity value $RH_{ENV}$; and a main control unit for communicating with and controlling the battery unit, the trigger, the infrared receiving device, the laser beam, the IO interface, and the temperature-humidity sensor, the leaf VPD value $VPD_{LEAF}$ calculated from the environmental temperature value $T_{ENV}$ and the environmental relative humidity value $RH_{ENV}$ is implemented to control plant cultivation.

According to an embodiment of the invention, the leaf VPD value $VPD_{LEAF}$ is calculated from the temperature value $T_{LEAF}$, the environmental temperature value $T_{ENV}$ and the environmental relative humidity value $RH_{ENV}$ by:

$$VPD_{LEAF} = 610.78e^{17.2694\frac{T_{LEAF}}{237.3+T_{LEAF}}} - 610.78e^{17.2694\frac{T_{ENV}}{237.3+T_{ENV}}} \times \frac{RH_{ENV}}{100},$$

$VPD_{LEAF}$ unit is in Pa, $T_{ENV}$ is temperature of the environment in degrees Celsius, $RH_{ENV}$ is relative humidity of the environment in % unit and e≈2.71828. According to an embodiment of the invention, the environment VPD value $VPD_{ENV}$ is calculated from environmental temperature value $T_{ENV}$ and the environmental relative humidity value $RH_{ENV}$ via: $VPD_{ENV} = 610.78e^{17.2694\frac{T_{ENV}}{237.3+T_{ENV}}}\left(1 - \frac{RH_{ENV}}{100}\right)$, $VPD_{ENV}$ unit is in Pa, $T_{ENV}$ is temperature of the environment in degrees Celsius, $RH_{ENV}$ is relative humidity of the environment in % unit and e≈2.71828.

According to an embodiment of the invention, the leaf VPD value $VPD_{LEAF}$ is calculated again after a predetermined time period with an updated temperature value $T_{LEAF}$, the leaf VPD value $VPD_{LEAF}$ is compared again with the second pre-determined VPD threshold value $VPD_{\theta 2}$ to adjust an VPD altering device. According to an embodiment of the invention, the VPD altering device is an air conditioner.

According to an embodiment of the invention, a networked VPD measuring and controlling device system for a plant cultivation environment is disclosed. The networked VPD measuring and controlling device system includes: a plurality of VPD measuring and controlling devices deployed at different locations inside the plant cultivation environment; at least one VPD altering unit deployed inside the plant cultivation environment; a computation module; each of the plurality of VPD measuring and controlling devices further includes: an infrared temperature senor, an environmental temperature sensor, and an environmental relative humidity sensor; and the plurality of VPD measuring and controlling devices, the at least one VPD altering unit, and the computation module are networked together. According to an embodiment of the invention, the networked VPD measuring and controlling device system is networked together via a wireless network. According to an embodiment of the invention, the networked VPD measuring and controlling device system for the plant cultivation environment further includes at least one wireless controller deployed outside the plant cultivation environment, the at least one wireless controller controls the plurality of VPD measuring and controlling devices and the at least one VPD altering units deployed inside the plant cultivation environment. According to an embodiment of the invention, the at least one VPD altering unit is an air conditioner. According to an embodiment of the invention, the at least one VPD altering unit is a humidifier. According to an embodiment of the invention, the at least one VPD altering unit is a dehumidifier. According to an embodiment of the invention, the at least one VPD altering unit is a heater.

BRIEF DESCRIPTION OF THE FIGURES

The invention will now be explained in more detail using exemplary embodiments and with references to the drawings, in which.

DETAILED DESCRIPTION OF PREFERRED EMBODIMENTS

Figure 1:
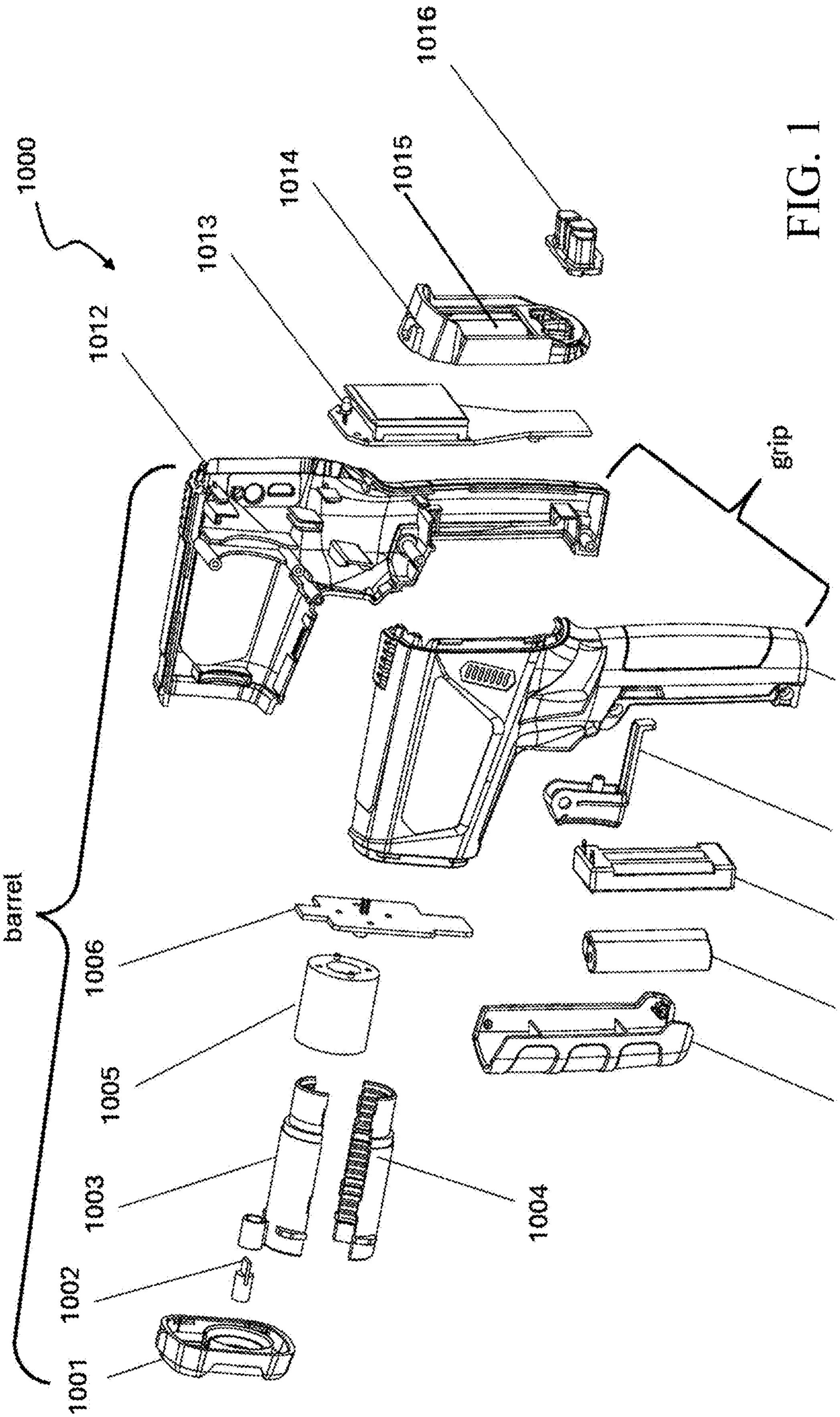
FIG. 1 is an exploded view of a hand-held vapor pressure deficit measuring device, according to an embodiment of the invention.

The invention is susceptible of many embodiments. Preferred embodiments are illustrated in the attached figures and explained below. Minor variations of the preferred embodiments are evident in the figures, but are substantially the same, with common or similar components and the same reference numbers, except as noted.

The saturation vapor pressure deficit of an air sample (sometimes "vapor pressure deficit, VPD" or just "saturation deficit" for short) is the difference between the saturation vapor pressure and the actual vapor pressure at temperature T, i.e., SVP (Saturation Vapor Pressure)−AVP (Actual Vapor Pressure). VPD is the difference between moisture that is currently in the environment air and how much moisture the environment air can hold at saturation, or dew point under certain conditions. In ecological problems, VPD is often regarded as a measure of the "drying power" of air, because it plays an important part in determining the relative rates of growth and transpiration in plants. In micrometeorology, the vertical gradient of saturation deficit is a measure of the lack of equilibrium between a wet surface and the air passing over it. Vapor Pressure Deficit ("VPD") plays a crucial role in plant indoor cultivation, especially high valued plants, such as cannabis.

The environment VPD can be calculated from environmental temperature value $T_{ENV}$ and the environmental relative humidity value $RH_{ENV}$. By definition, VPD=SVP (Saturation Vapor Pressure)−AVP (Actual Vapor Pressure), SVP is the "Saturation Vapor Pressure" and AVP is the "Actual Vapor Pressure".

$$SVP = 610.78e^{17.2694\frac{T_{ENV}}{237.3+T_{ENV}}},$$

wherein, 610.78, 17.2694 and 237.3 are constants, and $T_{ENV}$ is temperature of the environment in degrees Celsius.

$$AVP = 610.78e^{17.2694\frac{T_{ENV}}{237.3+T_{ENV}}}\frac{RH_{ENV}}{100},$$

wherein, $RH_{ENV}$ is the relative humidity of environment in % unit, and 610.78, 17.2694 and 237.3 are constants, $T_{ENV}$ is temperature of the environment in degrees Celsius.

$$\text{Environment } VPD = SVP - AVP = 610.78e^{17.2694\frac{T_{ENV}}{237.3+T_{ENV}}}\left(1 - \frac{RH_{ENV}}{100}\right),$$

wherein, $VPD_{ENV}$ unit is in Pa, $T_{ENV}$ is temperature of the environment in degrees Celsius. $RH_{ENV}$ is the relative humidity of environment in % unit, e≈2.71828.

The SVP value can be calculated by, for example, the following code:

```
/**********************VPD**************************/
double get_svp (double t)
{
  double svp, power;
  power = t / (t + 237.3) * 17.2694;
  svp = 610.78 * pow (2.71828, power);
  return svp;
}
```

The code shows the calculation of the saturated vapor pressure SVP (Saturation Vapor Pressure) from a temperature of the environment $T_{ENV}$. The unit is Pa. On the display, it is possible to display either Pa or kPa, or other units if appropriate.

According to another embodiment of the invention, the Leaf VPD can be calculated by following the steps below:

a. Obtaining real time temperature value $T_{LEAF}$, environment temperature value $T_{ENV}$ (° C.) and real time environmental relative humidity value $RH_{ENV}$, and obtaining Leaf Offset, which is defaulted to zero and can be set by the user within the recommended range: −10° C.~10° C.;

b. Calculating the leaf temperature $T_{LEAF}=T_{ENV}$+Leaf Offset, wherein T (° C.) is real time air temperature, $T_{LEAF}$ (° C.) is leaf temperature, Leaf Offset is the difference between the leaf and the air temperature, Leaf Offset=$T_{LEAF}-T_{ENV}$;

c. Calculating ASVP, which is the environment SVP, wherein $$ASVP = 610.78e^{17.2694\frac{T_{ENV}}{237.3+T_{ENV}}};$$

d. Calculating LSVP, which is the leaf SVP, wherein $$LSVP = 610.78e^{17.2694\frac{T_{LEAF}}{237.3+T_{LEAF}}};$$

e. Calculating leaf VPD, wherein Leaf VPD value $VPD_{LEAF}$=LSVP−(ASVP×RH/100);

f. Calculating real time Leaf VPD, wherein $$\text{Leaf } VPD \text{ value } VPD_{LEAF} = LSVP - ASVP \times RH/100 = 610.78e^{17.2694\frac{T_{LEAF}}{237.3+T_{LEAF}}} - 610.78e^{17.2694\frac{T_{ENV}}{237.3+T_{ENV}}} \times \frac{RH_{ENV}}{100},$$

wherein the unit of Leaf VPD value $VPD_{LEAF}$ is Pa, the unit of temperature is ° C., the unit of RH is %, and e≈2.71828.

VPD plays an important role in cannabis cultivation. Plants respond to changes in water availability in both their aerial and soil environments. The driving force of transpiration rate is the gradient in vapour pressure between the dry atmosphere and the wet interior of leaves, which is referred to as VPD as discussed above.

A high VPD indicates a hotter and drier environment, while a low VPD results from a cooler and more humid environment. Scientific studies have demonstrated that the cannabis is highly responsive to changes in VPD, and VPD has been identified as a critical factor influencing transpiration and stomatal conductance in crops including cannabis.

Figure 6:
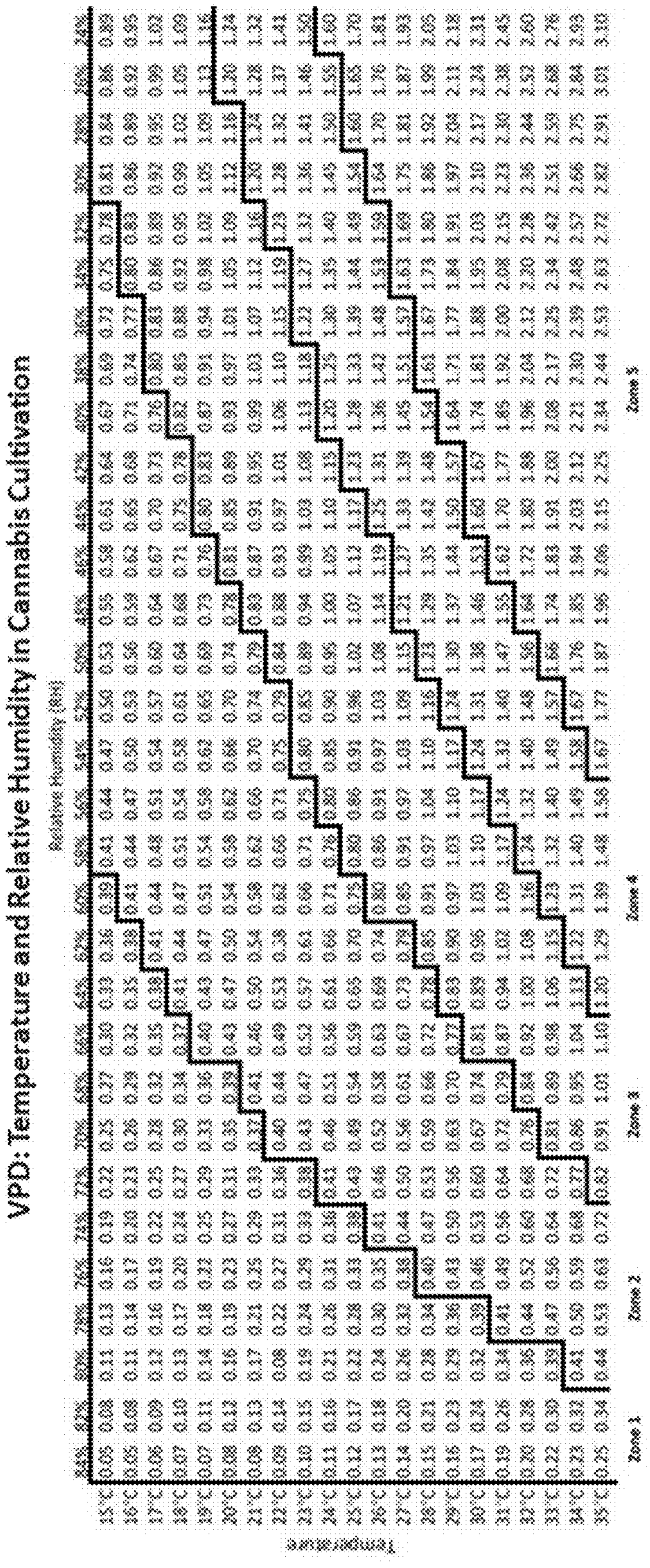
FIG. 6 is a chart illustrating the relationship among VPD, temperature and relative humidity in cannabis cultivation, according to an embodiment of the invention.

For cannabis growers with indoor grow tents or rooms with artificial lighting, in addition to temperature and relative humidity parameters, it is critical to take into consideration the importance of VPD and its impact on transpiration or nutrient uptake. For example, as illustrated in FIG. 6, in the chart depicting the relationship between temperature, humidity and VPD below, there are five zones: zone 1 through zone 5, with different combinations of temperature and relative humidity values. For example, zone 1: danger zone; zone 2: blue zone for low transpiration stage, propagation stage and early vegetative stage; zone 3: green zone for optimized healthy growth during transpiration stage, late vegetative state, and early flower stage; zone 4: yellow zone for high transpiration stage and late flower stage; zone 5: danger zone. Among these zones, zone 3 is the optimal zone with ideal combinations of temperature and relative humidity value for cannabis plants. For different stages, such as growth and flowering stages, temperature, relative humidity, and the recommended leaf VPD values are listed in the chart in FIG. 6.

Different VPD values are recommended for different stages of the plant. For example, for VPD value between 1.20 kPa and 1.60 kPa, which is considered relatively high, plants tend to open their stomata and release a considerable amount of water vapour into the environment to increase their transpiration. This increase in transpiration results in an increase in the plant's photosynthetic activity and will improve its overall growth during both growth and bloom. The optimal VPD range is between 0.80 kPa and 1.20 kPa. When the VPD is too high, the plant closes its stomata to avoid releasing excessive amount of the water vapor into the environment. Excessive transpiration causes dehydration. On the other hand, when VPD is too low, the atmosphere is already saturated and has reached the maximum water retention capacity, the plant will also close its stomata to avoid releasing too much water vapor into the atmosphere.

Decreased transpiration reduces photosynthesis, slowing the plant's development and lowering yield.

FIG. 1 is an exploded view of a hand-held vapor pressure deficit measuring and controlling device, according to an embodiment of the invention. An exploded view of a hand-held VPD measuring and controlling device 1000 for plant cultivation, for example, for indoor residential cannabis cultivation is illustrated in FIG. 1, the hand-held VPD measuring and controlling device is also called a VPD gun. According to an embodiment of the invention, the hand-held VPD measuring and controlling device 1000 is designed to resemble the shape of a pistol, or a handgun, with a grip, a muzzle, a barrel and a trigger. According to an embodiment of the invention, the hand-held VPD measuring and controlling device 1000 is designed in other shapes and configurations as well for convenience of usage. According to an embodiment of the invention, the hand-held VPD measuring and controlling device 1000 can be designed in shapes and configurations other than a pistol, or a handgun. In the illustration of the hand-held VPD measuring and controlling device 1000 in FIG. 1, a laser transmitter 1002 is implemented to emit an indicating laser beam along the direction of the barrel and out of the muzzle 1001, the indicating laser beam is pointed to the location where a temperature needs to be measured. The barrel body is provided with an infrared receiving module 1005, the infrared radiation emitted by the object to be measured is received by the infrared receiving module 1005 through the muzzle 1001, and the temperature of the position indicated by the handheld VPD measurement and control device 1000 is measured. In a plant cultivation environment, or more specifically, an indoor residential cannabis cultivation environment, for example, the location to be measured can be the surface of cannabis leaves. When the hand-held VPD measuring and controlling device 1000 points at the surface of cannabis leaves, the leaf temperature is measured and a leaf VPD $VPD_{LEAF}$ is calculated from the leaf temperature $T_{LEAF}$, the environmental temperature $T_{ENV}$ and the environmental relative humidity $RH_{ENV}$. In the discussions throughout this application, the plant cultivation environment can be an indoor residential cannabis cultivation environment. In addition, the plant cultivation environment can also be a cultivation environment for any other plants or vegetables, etc., indoor or outdoor.

According to an embodiment of the invention, the hand-held VPD measuring and controlling device does not always need to be held by a human user. Instead, the hand-held VPD measuring and controlling device is a mobile device which can also be deployed in the plant cultivation environment, or the indoor residential cannabis cultivation environment without being held by a user. According to an embodiment of the invention, the hand-held VPD measuring and controlling device is wirelessly networked within other similar devices, or other VPD altering devices and equipment, or other computer devices, or other mobile phone or tablet devices. Such networked devices and equipment can be controlled centrally by a server, or the controller's software and hardware can be distributed across the network. Details regarding such networked deployment will be discussed in the following figures and paragraphs.

According to an embodiment of the invention, the laser transmitter 1002 and the infrared receiving module 1005 are enclosed between the upper sleeve 1003 and the lower sleeve 1004. Both the laser transmitter 1002 and the infrared receiving module 1005 are properly aligned with the longitudinal axis of the barrel for better indicating the location of the measured infrared radiation. To assist the indicating the position to be measured, a laser beam indication is implemented according to an embodiment of the invention. The laser beam is emitted by the laser transmitter 1002, and the direction of the laser beam is parallel to the direction of receiving the infrared radiation, which is also parallel to the longitudinal axis of the barrel.

According to an embodiment of the invention, the infrared receiving module 1005 is electrically connected to and controlled by the infrared driver control board 1006 enclosed inside the hand-held VPD measuring and controlling device 1000. The infrared driver control board 1006 can be enclosed inside the barrel, or alternatively, in other parts of the hand-held VPD measuring and controlling device 1000. According to an embodiment of the invention, the laser transmitter 1002, the infrared receiving module 1005 and the infrared driver control board 1006 are all powered by batteries 1008 enclosed inside the grip, supported by the battery support 1009, and covered by the battery cover 1007. The batteries 1008, the laser transmitter 1002, and the infrared receiving module 1005 are all enclosed inside a pistol shaped enclosure, with left cover 1011 and right cover 1012 for proper protection. All objects with a temperature higher than absolute zero are constantly emitting infrared radiation energy into the environment. The amount of infrared radiation energy of an object and its distribution according to wavelength are closely related to its surface temperature. Therefore, by measuring the infrared energy radiated by a certain object, its surface temperature can be accurately measured. This is the objective basis on which infrared radiation temperature measurement is based. The infrared energy emitted by the object under test is focused on the infrared receiving module 1005 and converted into a corresponding electrical signal. The infrared signal is processed and converted by the infrared driver control board 1006 into the temperature value of the object under measurement.

According to an embodiment of the invention, on the top of the grip, a display screen 1015 is implemented for displaying control information and input/output of information. The display screen 1015 can be a touch screen, or alternatively, buttons 1016 are provided for control and input/output. The display screen 1015 is equipped with a display cover 1014 for protection and to avoid flare. A control board 1013 is implemented to control the display screen 1015, as well as the laser transmitter 1002, the trigger 1010 and all other electronic components of the hand-held VPD measuring and controlling device 1000. According to an embodiment of the invention, for example, the control board 1013 can be conveniently implemented behind the display screen 1015. The control board 1013 is the main control unit, which controls the indicating laser beam emission, measurement of temperature and humidity, as well as all screen displays, calculations and functions setting, etc. The trigger 1010, which functions as a control button, is conveniently located below the barrel and next to the grip for easier operation. For example, the trigger 1010 is pulled to start the emission of laser and the reception processing of the infrared. For example, the trigger 1010 is pulled to point the laser beam at a location where the temperature is to be measured. For example, the location where the temperature is to be measured is a location on the surface of a piece of cannabis leave. For example, the trigger 1010 is pulled to make a temperature measurement at the location where the laser is pointing at. The trigger 1010 can be pulled and/or pulled-and-held, for example, different combinations of the trigger operations are possible for additional control functionalities. The hand-held VPD measuring and controlling device 1000 also includes a temperature sensor for measuring environmental temperature $T_{ENV}$ and a humidity sensor for measuring environmental relative humidity $RH_{ENV}$. The hand-held VPD measuring and controlling device 1000 also includes additional components, such as LED lights 1017, a DC connector 1018 and a USB connector 1019, which will be discussed further in the following figures and paragraphs.

Figure 2A:
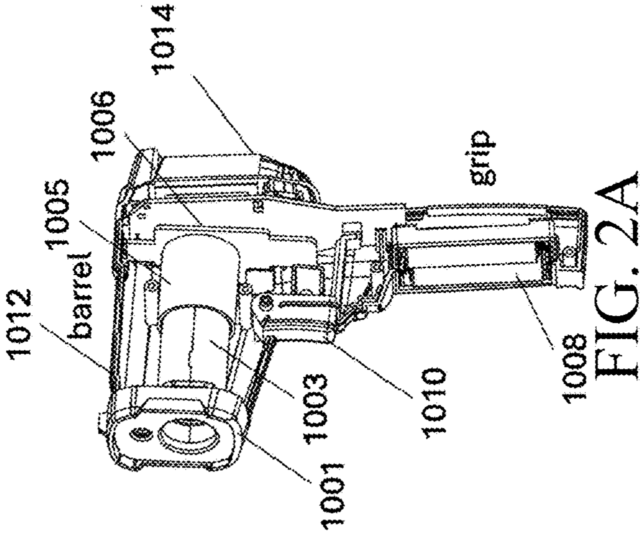
FIGS. 2A-2C are different views of a hand-held vapor pressure deficit measuring device, according to an embodiment of the invention.
Figure 2B:
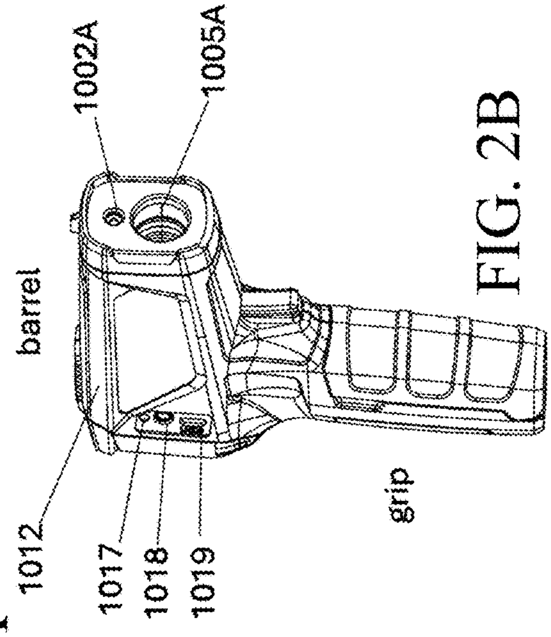
Figure 2C:
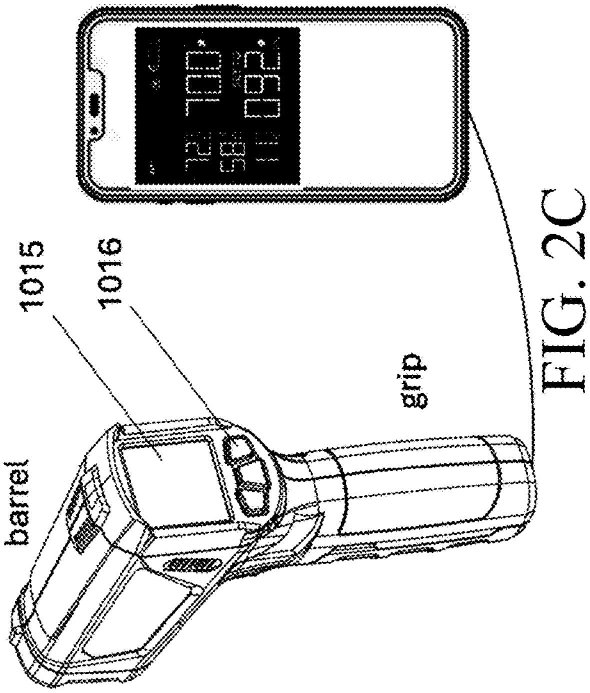

FIGS. 2A-2C are three different views of a hand-held vapor pressure deficit measuring and controlling device, according to an embodiment of the invention. In FIGS. 2A-2C, the components illustrated in FIG. 1 are properly assembled in a pistol shape. In FIG. 2A, the laser transmitter 1002 and the infrared receiving module 1005 are properly enclosed inside the barrel and maintained parallel to the barrel. In FIG. 2B, an opening 1002A at the end of the muzzle provide an exit for the laser beam emitted by the laser transmitter 1002. A corresponding opening 1005A close to the opening 1002A is provided for receiving the infrared light emitted by the target surface, for example, the surface of a cannabis leave. Proper alignments are conducted to ensure the infrared light is properly received by the opening 1005A, and by the infrared receiving module 1005 for accurate measurement. According to an embodiment of the invention, LED lights 1017, a DC connector 1018 and a USB connector 1019 are implemented on one side of the pistol enclosure of the hand-held VPD measuring and controlling device 1000. Other connectors can be implemented as well. In FIG. 2C, buttons 1016 and the display screen 1015 are illustrated. The buttons 1016 and the display screen 1015 are implemented to control and information IO. According to an embodiment of the invention, alternatively, the hand-held VPD measuring and controlling device 1000 can be connected to an external controller via USB connector 1019. The external controller can be a proprietary specialty external controller, or a personal mobile device, such as an iPhone, iPad, or Android phone or tablet, etc. The hand-held VPD measuring and controlling device 1000 can also be connected to an external controller via Wi-Fi, Bluetooth, or other wireless protocols. When connected to the external controller, all control and information input/output can be performed on the external controller, i.e., with appropriate Apps or other software installed. Further details regarding the wireless functions of the hand-held VPD measuring and controlling device 1000 will be discussed in the following figures and paragraphs.

Figure 3:
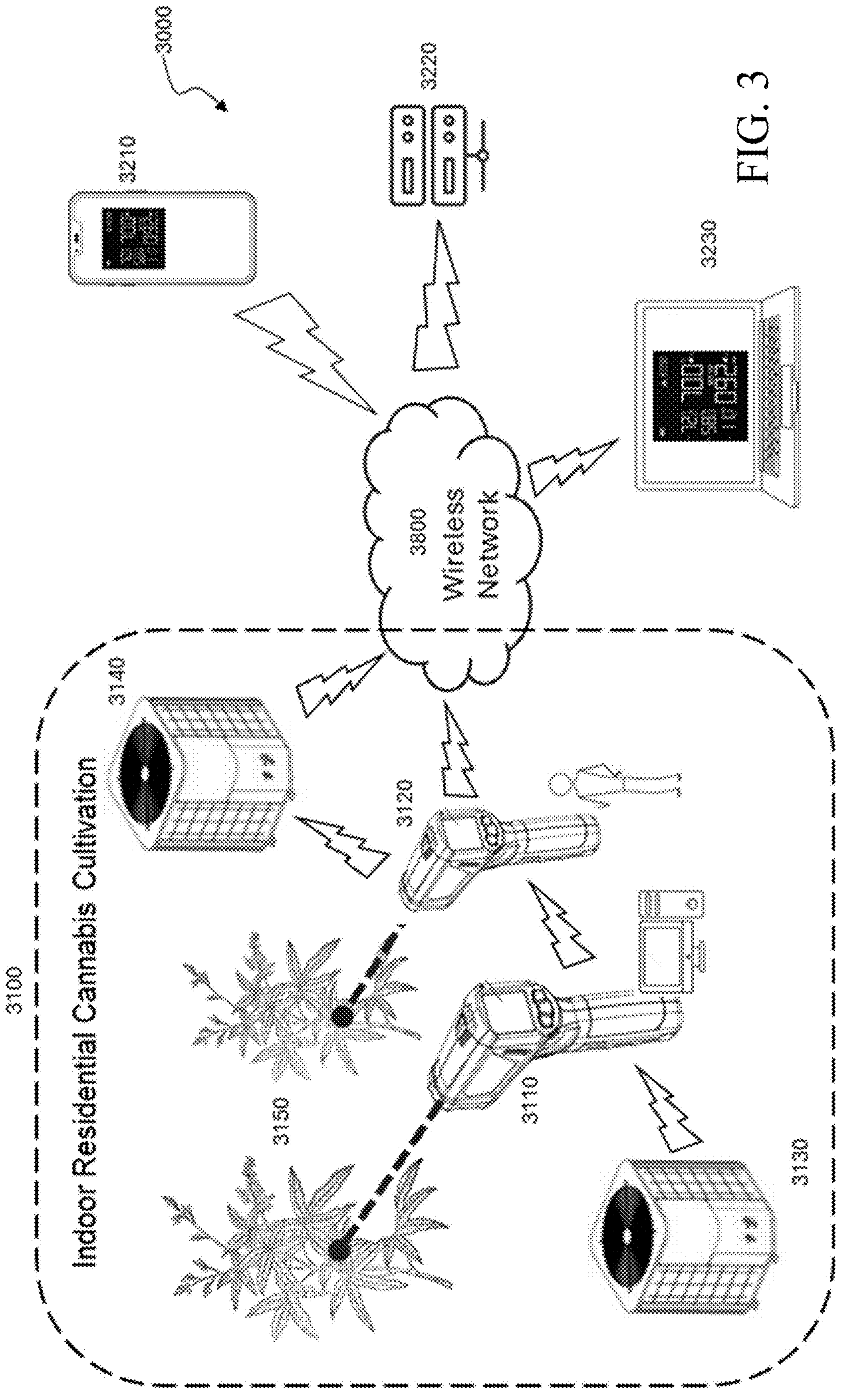
FIG. 3 is a schematic view of a system implementing multiple hand-held vapor pressure deficit measuring device, according to an embodiment of the invention.

FIG. 3 is a schematic view of a system implementing multiple hand-held vapor pressure deficit measuring and controlling devices, according to an embodiment of the invention. A system 3000 implementing multiple hand-held vapor pressure deficit measuring and controlling devices measures and controls the VPD inside a plant cultivation environment, or an indoor residential cannabis cultivation environment 3100 for optimized cannabis cultivation yield. The system 3000 is a wirelessly networked system with a plurality of computing devices, such as personal touch screen devices 3210, personal computer or laptop 3230, and servers 3220. The plurality of computing devices can be situated outside the plant cultivation environment, or the indoor residential cannabis cultivation environment 3100. Cannabis 3150, or other plants, are enclosed and grown inside the indoor residential cannabis cultivation environment 3100, which is, for example, a tent, or a room, or other space enclosures. Together with the cannabis 3150 inside the indoor residential cannabis cultivation environment 3100, a plurality of VPD altering equipment 3130 and 3140 are implemented to optimize the VPD inside the indoor residential cannabis cultivation environment 3100. Such VPD altering equipment 3130 and 3140 include, but is not limited to, air conditioners, heaters, humidifiers, and dehumidifiers. The VPD altering equipment 3130 and 3140 alters the VPD value inside the indoor residential cannabis cultivation environment 3100 by altering the corresponding temperature, or humidity, or both inside the indoor residential cannabis cultivation environment 3100.

According to an embodiment of the invention, a plurality of hand-held VPD measuring and controlling devices 3110 and 3120 are implemented inside the plant cultivation environment, or the indoor residential cannabis cultivation environment 3100 for measuring environmental temperature $T_{ENV}$, leaf temperature $T_{LEAF}$, and environmental relative humidity $RH_{ENV}$, Leaf VPD value $VPD_{LEAF}$, environmental VPD value $VPD_{ENV}$. According to an embodiment of the invention, the plurality of hand-held VPD measuring and controlling devices 3110 and 3120 are wirelessly networked via 3800 tother with the VPD altering equipment 3140 and 3150 inside the indoor residential cannabis cultivation environment 3100, as well as the plurality of computing devices either inside or outside the indoor residential cannabis cultivation environment 3100. The test data of hand-held VPD measuring and controlling device is transmitted to multiple computing devices or VPD conversion devices to control VPD conversion devices 3140 and 3150 in the indoor residential cannabis cultivation environment 3100 to achieve the best cannabis cultivation environment condition within 3100.

One of the hand-held VPD measuring and controlling devices, for example 3110, can be pointed at the surface of a piece of cannabis leaf to measure the leaf temperature $T_{LEAF}$. For example, when the trigger 1010 is pulled, the laser beam emitted by the laser transmitter 1002 is shot at the leaf for alignment and at the same time, infrared light emitted by the leaf position indicated by the laser beam is received, the leaf temperature $T_{LEAF}$ is measured and transmitted to other networked devices or equipment, if necessary, in the system 3000. When the corresponding leaf temperature $T_{LEAF}$, environmental temperature $T_{ENV}$ and environmental relative humidity $RH_{ENV}$ are also properly measured by the hand-held VPD measuring and controlling devices, the leaf VPD value $VPD_{LEAF}$ can be calculated. The leaf VPD value $VPD_{LEAF}$ can also be transmitted to other networked devices or equipment in the system 3000. When $VPD_{LEAF}$ is determined by one of the networked devices to be outside the optimal range, either above or below thresholds, at least one of the VPD altering equipment 3130 and 3140 inside the indoor residential cannabis cultivation environment 3100 are started to adjust temperature, relative humidity, or both, inside the indoor residential cannabis cultivation environment 3100 to properly alter VPD values, both the environmental VPD value $VPD_{ENV}$ and the leaf VPD value $VPD_{LEAF}$.

In the same way, the trigger 1010 can be pulled again to take another measurement of the leaf temperature $T_{LEAF}$ and the leaf VPD value $VPD_{LEAF}$ can be calculated again. Both the leaf temperature $T_{LEAF}$ and the leaf VPD value $VPD_{LEAF}$ can be transmitted over the wireless network to other networked devices and equipment again. If it is determined that the leaf VPD value $VPD_{LEAF}$ is within the optimal range, then if the VPD altering equipment that has been started is still running, then the VPD altering equipment is stopped. If there is no VPD altering equipment running, then no action is taken. The calculation and control decision can be conducted at any of the network devices with sufficient computation power. Such calculation and control can either be conducted centrally at a server, for example, 3220, or individually at any networked devices or equipment, for example, 3120 or 3140, as long as all devices and equipment are properly coordinated.

According to an embodiment of the invention, a user manually uses the hand-held VPD measuring and controlling device to get a new $T_{LEAF}$ reading each time, so while the $T_{ENV}$, $RH_{ENV}$, and $VPD_{ENV}$ of the hand-held VPD measuring and controlling device can be constantly passively updated to control an environmental device, the $T_{LEAF}$ can only be updated each time the device is physically used, i.e., by pulling the trigger 1010, or pushing of buttons. The user takes the $T_{LEAF}$ that is measured, subtracted by the $T_{ENV}$ to get the Leaf Offset, and then we're using this Leaf Offset number against the current $T_{ENV}$ number to calculate $T_{LEAF}$ and $VPD_{LEAF}$. For example, if the hand-held VPD measuring and controlling device measures $T_{LEAF}$ as 79° F. and $T_{ENV}$ as 77° F., then the Leaf Offset is equal to 2° F. As the $T_{ENV}$ fluctuates throughout the day, $T_{LEAF}$ is set to: $T_{LEAF}=T_{ENV}+2°$ F. until the Leaf Offset is otherwise manually changed.

According to an embodiment of the invention, the measurement of leaf temperature $T_{LEAF}$ and leaf VPD value $VPD_{LEAF}$, as well as other parameters, such as environmental relative humidity $RH_{ENV}$ and environmental temperature $T_{ENV}$, can be periodically conducted by a caregiver of the indoor residential cannabis cultivation environment 3100, or alternatively, can be automatically controlled by Apps or software installed on at least one of the networked devices or equipment. According to an embodiment of the invention, hand-held VPD measuring and controlling device 1000 can be fixed inside the indoor residential cannabis cultivation environment 3100 for long term monitoring of leaf temperature $T_{LEAF}$ and leaf VPD value $VPD_{LEAF}$. More than one VPD measuring and controlling devices 3120 and 3110 can be deployed inside the indoor residential cannabis cultivation environment 3100 at different locations for long term monitoring of leaf temperature $T_{LEAF}$ and leaf VPD value $VPD_{LEAF}$. Multiple VPD measuring and controlling devices 3110 and 3120 can be controlled wirelessly and remotely outside the indoor residential cannabis cultivation environment 3100.

According to an embodiment of the invention, the environmental devices, i.e., VPD related products, such as VPD altering products, VPD heaters, VPD air conditioners, VPD humidifiers, and VPD dehumidifiers, typically come with the temperature and humidity sensors to monitor $T_{ENV}$, $RH_{ENV}$, and $VPD_{ENV}$. When these environmental devices are connected, an update of the Leaf Offset is conducted, for example by the hand-held vapor pressure deficit measuring and controlling device. After such an update, all devices in the network can provide an accurate $VPD_{LEAF}$ reading.

Figure 4:
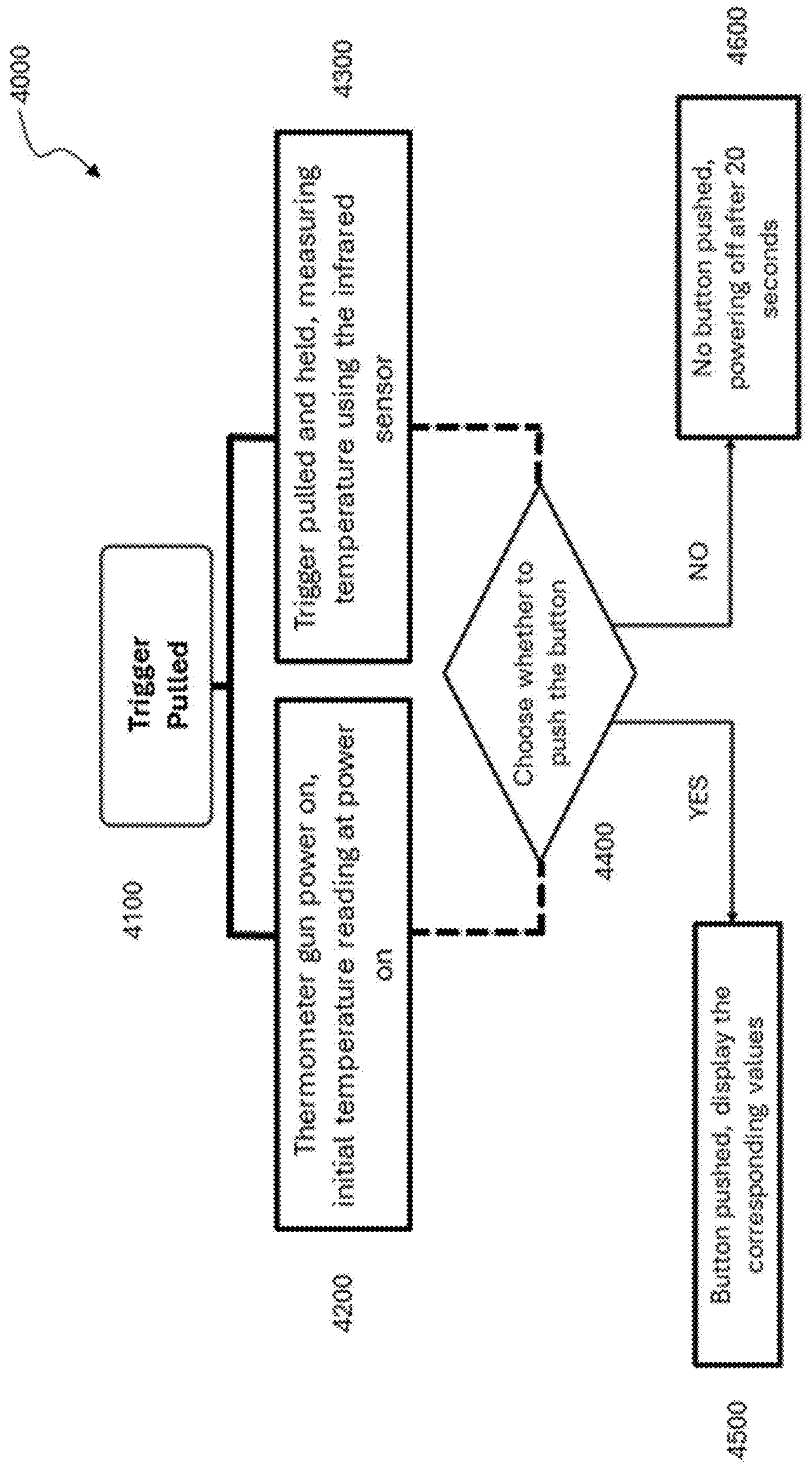
FIG. 4 is a functional flowchart of a hand-held vapor pressure deficit measuring device, according to an embodiment of the invention.

FIG. 4 is a functional flowchart of a hand-held vapor pressure deficit measuring and controlling device, according to an embodiment of the invention. An example of the functional flowchart 4000 of a hand-held vapor pressure deficit measuring and controlling device is illustrated in FIG. 4. In this example, when the trigger is pulled at step 4100, the hand-held vapor pressure deficit measuring and controlling device, or the VPD gun, is powered on, an initial temperature is measured at step 4200. The laser transmitter 1002 generates a laser beam, and when the laser beam is aimed at the surface of the cannabis leaf, the leaf temperature value $T_{LEAF}$, the environmental temperature value $T_{ENV}$, the environmental relative humidity value $T_{ENV}$, the leaf VPD value $VPD_{LEAF}$ and the environmental VPD value $VPD_{ENV}$ are measured at step 4200. When the trigger is pulled and held, the leaf temperature value $T_{LEAF}$, the environmental temperature value $T_{ENV}$, the environmental relative humidity value $T_{ENV}$, the leaf VPD value $VPD_{LEAF}$ and the environmental VPD value $VPD_{ENV}$ are measured continuously and in real time at step 4300. Then in the next step 4400, if the button 1016 is pressed, the following parameters and conditions can be set and changed in step 4500: the Emissivity values, display temperature display units (switching between ° C. and ° F.), etc. In addition, manual calibration and viewing of recent test data, etc. can also be performed in step 4500. Otherwise, if no buttons are pushed, the VPD gun is powered off in 20 seconds at step 4600.

Figure 5C:
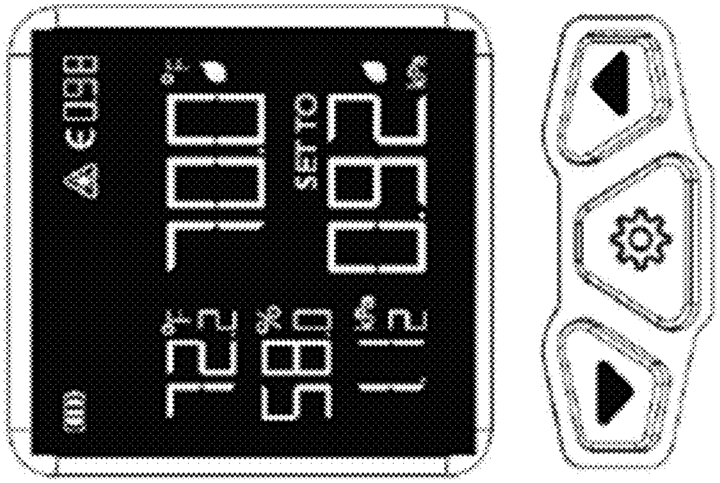
FIGS. 5A-5C are a schematic view of the display screen of a hand-held vapor pressure deficit measuring device, according to an embodiment of the invention.
Figure 5B:
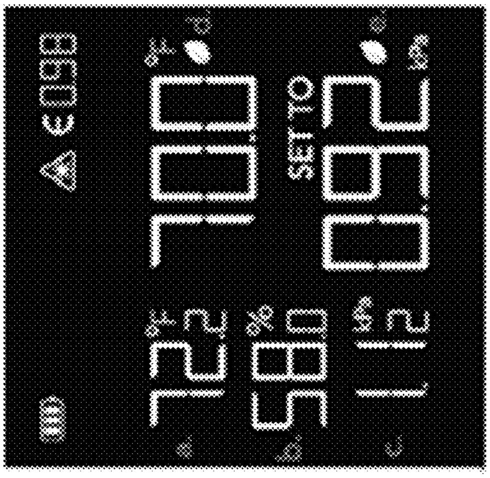
Figure 5A:
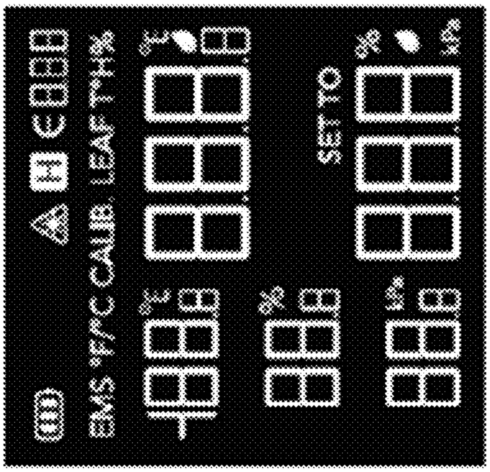

FIGS. 5A-5C are a schematic view of the display screen of a hand-held vapor pressure deficit measuring and controlling device, according to an embodiment of the invention. Information that can be displayed in the display screen include, for example, temperature, relative humidity. As illustrated in FIG. 5B, for example, (a.) is Ambient Temperature, (b.) is Ambient Humidity, (c.) is environment VPD, (d.) is Measure Leaf Temperature, and (e.) is Leaf VPD. FIG. 5C also illustrates the buttons below the display screen for controlling and input/output information on the display screen above it.

FIG. 6 is a chart illustrating the relationship among VPD, temperature and relative humidity in cannabis cultivation, according to an embodiment of the invention. As illustrated in FIG. 6, in the chart depicting the relationship between temperature, humidity and VPD below, there are five zones: zone 1 through zone 5, with different combinations of temperature and relative humidity values. For example, zone 1: danger zone; zone 2: blue zone for low transpiration stage, propagation stage and early vegetative stage; zone 3: green zone for optimized healthy growth during transpiration stage, late vegetative state, and early flower stage; zone 4: yellow zone for high transpiration stage and late flower stage; zone 5: danger zone. Among these zones, zone 3 is the optimal zone with ideal combinations of temperature and relative humidity value for cannabis plants. For different stages, such as growth and flowering stages, temperature, relative humidity, and the recommended leaf VPD values are listed in the chart in FIG. 6.

Controlling the environment via VPD that only caters to a specific consumer market, such as the indoor residential cannabis cultivation market, is relatively new. The high cost of setting up an indoor residential cannabis cultivation room or tent has long prevented the market from developing any specialty devices until recently, with the introduction of legalized residential indoor cannabis cultivation across the nation. When combined with the high cost of legally purchasing cannabis, this has led to the rise of consumers looking to start their own residential indoor cannabis cultivation. Financially, with each plant grown having a market value of on average $200-$1000, residential growers are now willing to spend much more on specialty indoor grow devices to improve their plant quality as they can often recapture the cost of expensive indoor cultivation equipment within 3-6 months. This has led to a push for better indoor cultivation equipment to be developed.

The hand-held VPD measuring and controlling device for indoor residential cannabis cultivation disclosed herein is the first instant VPD measuring and controlling device on the market and compliments all of the inventor's other VPD related products, such as VPD altering products, VPD heaters, VPD air conditioners, VPD humidifiers, and VPD dehumidifiers, as it is able to provide precise leaf temperature values $T_{LEAF}$ to calculate leaf VPD value $VPD_{LEAF}$. It is novel to the market to use ambient temperature (environmental temperature) $T_{ENV}$ and ambient relative humidity (environmental relative humidity) $RH_{ENV}$ to calculate environment VPD value $VPD_{ENV}$, and to use the environmental temperature value $T_{ENV}$, the environmental relative humidity value $RH_{ENV}$ with the leaf temperature $T_{LEAF}$ to calculate leaf VPD value $VPD_{LEAF}$. Significant redesign of the hardware, firmware, and software are performed to invent the hand-held VPD measuring and controlling device for indoor residential cannabis cultivation disclosed herein.

Other and various embodiments within the scope of the invention will be readily evident to practitioners skilled in the art, from specification, figures and claims that follow.

What is claimed is:

1. A hand-held vapor pressure deficit (VPD) measuring and controlling device for plant cultivation, the hand-held VPD measuring and controlling device comprising:

a device body with a barrel, a handle and a trigger;

a screen for displaying information on one end of the barrel of the device body;

a control module with a processing unit located inside the device body;

a laser beam transmitter emitting a laser beam located inside the device body, wherein the direction of the laser beam emitted by the laser beam transmitter is parallel to the direction of the barrel of the device body;

an infrared temperature sensor for measuring a temperature value at a location pointed by the laser beam, wherein when the trigger is pulled, the temperature value $T_{LEAF}$ at the location pointed by the laser beam is measured by the infrared temperature sensor and the temperature value $T_{LEAF}$ is transmitted to the control module in real time;

an environmental temperature-humidity sensor for sensing an environmental temperature value $T_{ENV}$ and an environmental relative humidity value $RH_{ENV}$ within a plant cultivation environment, wherein the environmental temperature value $T_{ENV}$ and the environmental relative humidity value $RH_{ENV}$ are transmitted to the control module in real time, and wherein a leaf VPD value $VPD_{LEAF}$ is calculated from the temperature value $T_{LEAF}$, the environmental temperature value $T_{ENV}$ and the environmental relative humidity value $RH_{ENV}$ by the processing unit of the control module, wherein an environmental VPD value $VPD_{ENV}$ is calculated from the environmental temperature value $T_{ENV}$ and the environmental relative humidity value $RH_{ENV}$ by the processing unit of the control module;

wherein the temperature value $T_{LEAF}$, the environmental temperature value $T_{ENV}$, the environmental relative humidity value $RH_{ENV}$, the leaf VPD value $VPD_{LEAF}$, the environmental VPD value $VPD_{ENV}$ are displayed on the screen.

2. The hand-held VPD measuring and controlling device for plant cultivation of claim 1, further comprises:

a wireless module for wirelessly communicating information with other devices.

3. The hand-held VPD measuring and controlling device for plant cultivation of claim 2, wherein one of heaters, dehumidifiers, humidifiers, or air conditioners inside the plant cultivation environment can be selected on a remote controller to be remotely controlled.

4. The hand-held VPD measuring and controlling device for plant cultivation of claim 3, wherein the leaf VPD value $VPD_{LEAF}$ is compared with a pre-determined VPD threshold value $VPD_{\theta}$ to determine running modes of heaters, dehumidifiers, humidifiers, or air conditioners inside the plant cultivation environment to adjust the leaf VPD value $VPD_{LEAF}$ within the plant cultivation environment, and wherein the remote controller wirelessly transmits control signals to heaters, dehumidifiers, humidifiers, or air conditioners inside the plant cultivation environment to adjust the environmental temperature value $T_{ENV}$, or the environmental relative humidity value $RH_{ENV}$ within the plant cultivation environment.

5. The hand-held VPD measuring and controlling device for plant cultivation of claim 2, wherein when the trigger is triggered, an updated temperature value $T_{LEAF}$ IS measured, wherein the temperature-humidity sensor senses an updated environment temperature value $T_{ENV}$ and an updated environmental relative humidity value $RH_{ENV}$ within the plant cultivation environment;

wherein the updated temperature value $T_{LEAF}$, the updated environmental temperature value $T_{ENV}$ and the updated environmental relative humidity value $RH_{ENV}$ are transmitted to the control module; and wherein an updated leaf VPD value $VPD_{LEAF}$ is calculated from the updated temperature value $T_{LEAF}$, the updated environmental temperature value $T_{ENV}$ and the updated environmental relative humidity value $RH_{ENV}$ by the processing unit of the control module.

6. The hand-held VPD measuring and controlling device for plant cultivation of claim 5, wherein the updated leaf VPD value $VPD_{LEAF}$ is compared with the pre-determined VPD threshold value $VPD_{\theta}$ again to adjust the running modes of the heaters, dehumidifiers, humidifiers, or air conditioners inside the plant cultivation environment to adjust the leaf VPD value $VPD_{LEAF}$ within the plant cultivation environment; and wherein the remote controller wirelessly transmits control signals to the heaters, dehumidifiers, humidifiers, or air conditioners inside the plant cultivation environment to adjust the environmental temperature value $T_{ENV}$, or the environmental relative humidity value $RH_{ENV}$ within the plant cultivation environment.

7. The hand-held VPD measuring and controlling device for plant cultivation of claim 1, further comprises: a connector for connecting with an external digital device with touch screen, wherein the hand-held VPD measuring and controlling device can be controlled by the external digital device.

8. A pistol shaped hand-held vapor pressure deficit (VPD) measuring and controlling device for plant cultivation, the pistol shaped hand-held VPD measuring and controlling device comprising:

a muzzle, a barrel, a grip and a trigger;

a battery unit for providing electric power to the pistol shaped hand-held VPD measuring and controlling device, wherein the battery unit is located in the grip of the pistol shaped hand-held VPD measuring and controlling device;

an infrared receiving device for measuring a temperature value $T_{LEAF}$, wherein the infrared receiving device receiving infrared beams through the muzzle and along a direction of the barrel of the pistol shaped hand-held VPD measuring and controlling device;

a laser transmitter implemented to emit a laser beam parallel to the direction of the barrel and passes through the muzzle, wherein the infrared receiving device measures the temperature value $T_{LEAF}$ at where the laser beam is pointed to;

an IO interface for input and output of control information and status information;

a temperature-humidity sensor for sensing an environmental temperature value $T_{ENV}$ and an environmental relative humidity value $RH_{ENV}$ within a plant cultivation environment, wherein a leaf VPD value $VPD_{LEAF}$ is calculated from the environmental temperature value $T_{ENV}$ and the environmental relative humidity value $RH_{ENV}$; and a main control unit for communicating with and controlling the battery unit, the trigger, the infrared receiving device, the laser beam, the IO interface, and the temperature-humidity sensor, wherein, the leaf VPD value $VPD_{LEAF}$ calculated from the environmental temperature value $T_{ENV}$ and the environmental relative humidity value $RH_{ENV}$ is implemented to control plant cultivation.

9. The pistol shaped hand-held VPD measuring and controlling device for plant cultivation of claim 8, wherein the leaf VPD value $VPD_{LEAF}$ is calculated from the temperature value $T_{LEAF}$, the environmental temperature value $T_{ENV}$ and the environmental relative humidity value $RH_{ENV}$ by:

$$VPD_{LEAF} = 610.78e^{17.2694\frac{T_{LEAF}}{237.3+T_{LEAF}}} - 610.78e^{17.2694\frac{T_{ENV}}{237.3+T_{ENV}}} \times \frac{RH_{ENV}}{100},$$

wherein, $VPD_{LEAF}$ unit is in Pa, $T_{ENV}$ is temperature of the environment in degrees Celsius, $RH_{ENV}$ is relative humidity of the environment in % unit and e≈2.71828.

10. The pistol shaped hand-held VPD measuring and controlling device for plant cultivation of claim 9, wherein the environment VPD value $VPD_{ENV}$ is calculated from environmental temperature value $T_{ENV}$ and the environmental relative humidity value $RH_{ENV}$ via:

$$VPD_{ENV} = 610.78e^{17.2694\frac{T_{ENV}}{237.3+T_{ENV}}}\left(1 - \frac{RH_{ENV}}{100}\right),$$

wherein, $VPD_{ENV}$ unit is in Pa, $T_{ENV}$ is temperature of the environment in degrees Celsius, $RH_{ENV}$ is relative humidity of the environment in % unit and e≈2.71828.

11. The pistol shaped hand-held VPD measuring and controlling device for plant cultivation of claim 9, wherein the updated leaf VPD value $VPD_{LEAF}$ is compared with a second pre-determined VPD threshold value $VPD_{\theta 2}$ to adjust an VPD altering device.

12. The pistol shaped hand-held VPD measuring and controlling device for plant cultivation of claim 11, wherein the leaf VPD value $VPD_{LEAF}$ is calculated again after a predetermined time period with an updated temperature value $T_{LEAF}$, wherein the leaf VPD value $VPD_{LEAF}$ is compared again with the second pre-determined VPD threshold value $VPD_{\theta 2}$ to adjust an VPD altering device.

13. The pistol shaped hand-held VPD measuring and controlling device for plant cultivation of claim 11, wherein the VPD altering device is an air conditioner.

14. A networked vapor pressure deficit (VPD) measuring and controlling device system for a plant cultivation environment, the networked VPD measuring and controlling device system comprising:

a plurality of VPD measuring and controlling devices deployed at different locations inside the plant cultivation environment;

at least one VPD altering unit deployed inside the plant cultivation environment;

a computation module;

wherein, each of the plurality of VPD measuring and controlling devices further comprises:

an infrared temperature senor, an environmental temperature sensor, and an environmental relative humidity sensor; and wherein, the plurality of VPD measuring and controlling devices, the at least one VPD altering unit, and the computation module are networked together.

15. The networked VPD measuring and controlling device system for the plant cultivation environment of claim 14, wherein the networked VPD measuring and controlling device system is networked together via a wireless network.

16. The networked VPD measuring and controlling device system for the plant cultivation environment of claim 15, further comprises at least one wireless controller deployed outside the plant cultivation environment, wherein the at least one wireless controller controls the plurality of VPD measuring and controlling devices and the at least one VPD altering units deployed inside the plant cultivation environment.

17. The networked VPD measuring and controlling device system for the plant cultivation environment of claim 14, wherein the at least one VPD altering unit is an air conditioner.

18. The networked VPD measuring and controlling device system for the plant cultivation environment claim 14, wherein the at least one VPD altering unit is a humidifier.

19. The networked VPD measuring and controlling device system for an plant cultivation environment claim 14, wherein the at least one VPD altering unit is a dehumidifier.

20. The networked VPD measuring and controlling device system for the plant cultivation environment claim 14, wherein the at least one VPD altering unit is a heater.

* * * * *